United States Patent [19]

Ramseyer et al.

[11] Patent Number: 5,515,842
[45] Date of Patent: May 14, 1996

[54] INHALATION DEVICE

[75] Inventors: Markus Ramseyer, Thun; René Gabriel, Gurzelen; Peter Michel, Burgdorf, all of Switzerland

[73] Assignee: Disetronic AG, Burgdorf, Switzerland

[21] Appl. No.: 287,158

[22] Filed: Aug. 8, 1994

[30] Foreign Application Priority Data

Aug. 9, 1993 [CH] Switzerland .......................... 02369/93

[51] Int. Cl.$^6$ .................................................. A61M 11/00
[52] U.S. Cl. .................................. 128/200.18; 128/200.14
[58] Field of Search .................. 128/200.14, 200.18, 128/200.21, 200.22, 200.23, 203.12, 200.16, 203.21

[56] References Cited

U.S. PATENT DOCUMENTS

| | | | |
|---|---|---|---|
| 4,790,479 | 12/1988 | Matsumoto et al. | 128/200.16 |
| 4,877,989 | 10/1989 | Drews et al. | 128/200.16 |
| 5,221,025 | 6/1993 | Privas | 128/200.23 |
| 5,347,998 | 9/1994 | Hodson et al. | 128/200.23 |

FOREIGN PATENT DOCUMENTS

| | | | |
|---|---|---|---|
| 4034025 | 10/1990 | Germany | 128/203.21 |
| 9416759 | 8/1994 | WIPO | 128/203.12 |

*Primary Examiner*—Edgar S. Burr
*Assistant Examiner*—V. Srivastava
*Attorney, Agent, or Firm*—Walter C. Farley

[57] ABSTRACT

A medical inhaler generates an aerosol of pharmaceutically effective medication to be absorbed by the respiratory tract of a patient includes a reservoir (1) of liquid medication, a conveyor (2) to expel the liquid from the reservoir, an atomizing vibrator (3) and a feed line (4) to conduct the liquid between the reservoir and the vibrator. The conveyor and the vibrator can be controlled by a process controller (15) which can include a microprocessor. Discharge of liquid medicine is both coordinated with the vibrator and accurately dosable and achieves optimal atomization of the medicine.

15 Claims, 4 Drawing Sheets

INHALATION DEVICE

FIELD OF THE INVENTION

This invention relates to a medical inhaler to generate an aerosol to be absorbed by the respiratory tract of a patient, the aerosol including pharmaceutically active substances.

BACKGROUND OF THE INVENTION

A device of this general type is known from European patent document B10,258,637. In that device, dosing is implemented by manually pushing a button so that a cartridge of liquid containing the medicine is somewhat compressed and, as a result, a given quantity of medicine is fed in the form of droplets to an atomizer. In such manual dosage the compression applied to the cartridge can vary within wide limits and, accordingly, the dispensed quantity of medicine cannot be predetermined. When the discharge rate of the medicine liquid is excessive, then in spite of the desired droplet form, there will be a continuous liquid jet and as a result the liquid medicine no longer can be deposited on the atomizer dish. Another drawback of this known inhaling device is that dosage is restricted to a single droplet, that is to about 20 μltr (microliters).

SUMMARY OF THE INVENTION

An object of the invention is to provide an inhaler allowing optimal medicine atomization by means of a controlled dispensation of liquid medicine coordinated with an atomizing vibrator.

Further objects of the invention are to minimize the dead space in the liquid-medicine feed to the atomizer, further preventing the liquid medicine from evaporating or crystallizing on its path to this atomizer, improving the storage properties of the liquid medicine and configuring the inhaler as a module in order that different medicines may be administered with the same device.

The inhaler of the invention makes possible different kinds of discharge depending on application. By suitably controlling the conveyor means, any of a) individual droplets, b) a sequence of discrete droplets, or c) a continuous, fine jet of liquid (at a defined flow) may be fed to the vibrator.

Preferably "droplet units" of 10 to 20 μltr are dripped onto the atomizer dish. Preferably approximately 50 μltr of liquid is conveyed and atomized within 1.5 sec. Depending on medicine, however, droplets between 3 and 40 μltr may be advantageous.

The advantage offered by the invention essentially may be construed as an exceedingly accurate and pre-definable dosage of lung-destined medicine being made possible thanks to the invention's controlled coordination between liquid feed to the atomizer and this atomizer's activation.

BRIEF DESCRIPTION OF THE DRAWINGS

The invention as well as further developments are described below with reference to the following drawings showing several embodiments wherein.

DESCRIPTION OF THE PREFERRED EMBODIMENTS

Figure 1:
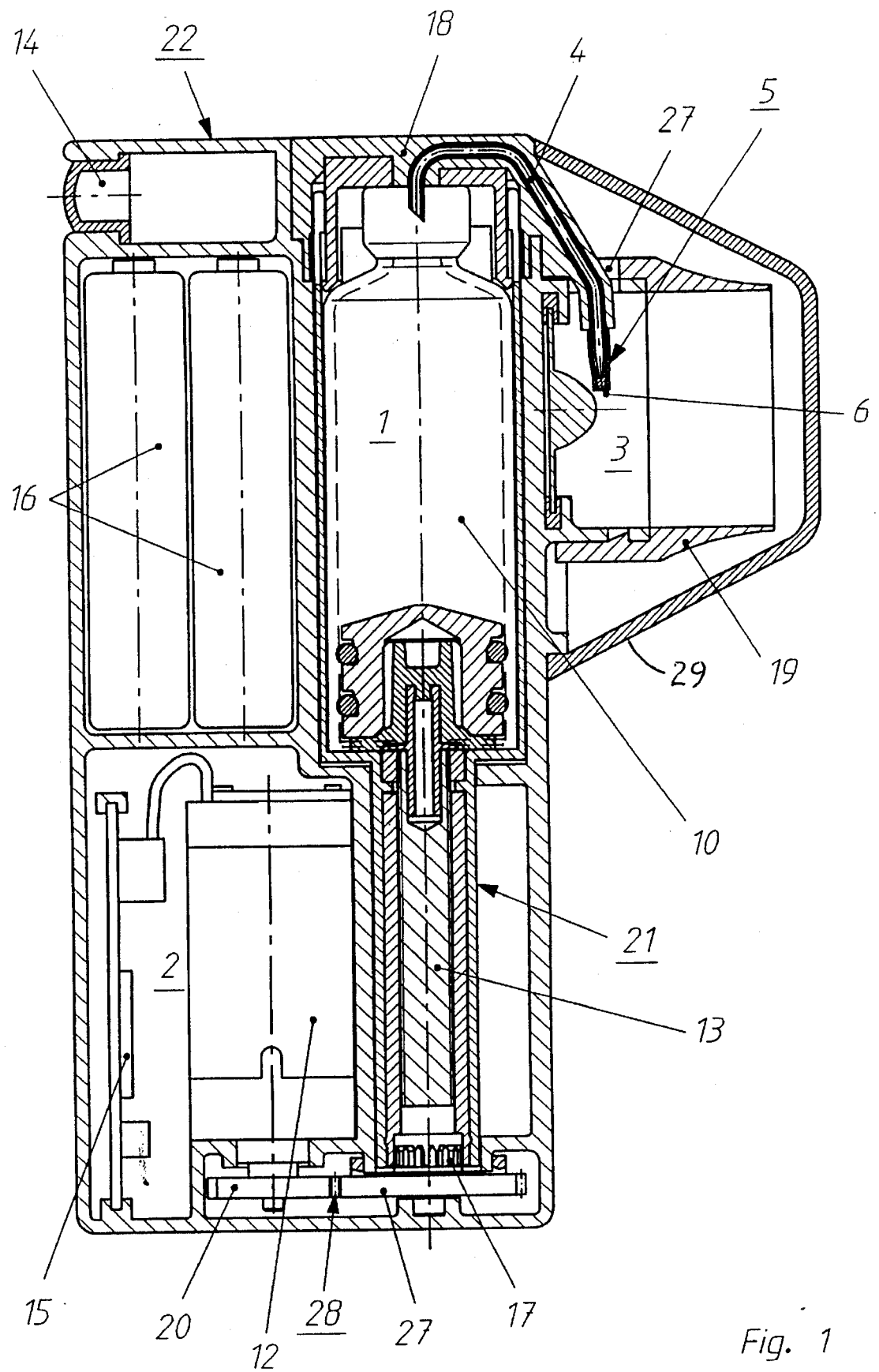
FIG. 1 is a side elevation, in section, of a dosing unit of the inhaler in accordance with the invention when in the inactive storage state.

The medical inhaler shown in FIG. 1 has a separate dosing unit 21, which can be inserted into a housing 22 which also receives a conveyor 2, a vibrator 3 and a process control means 15, the dosing unit being removable at will. A cover 29 snaps on to the front of housing 22 and is removable before use.

Figure 2:
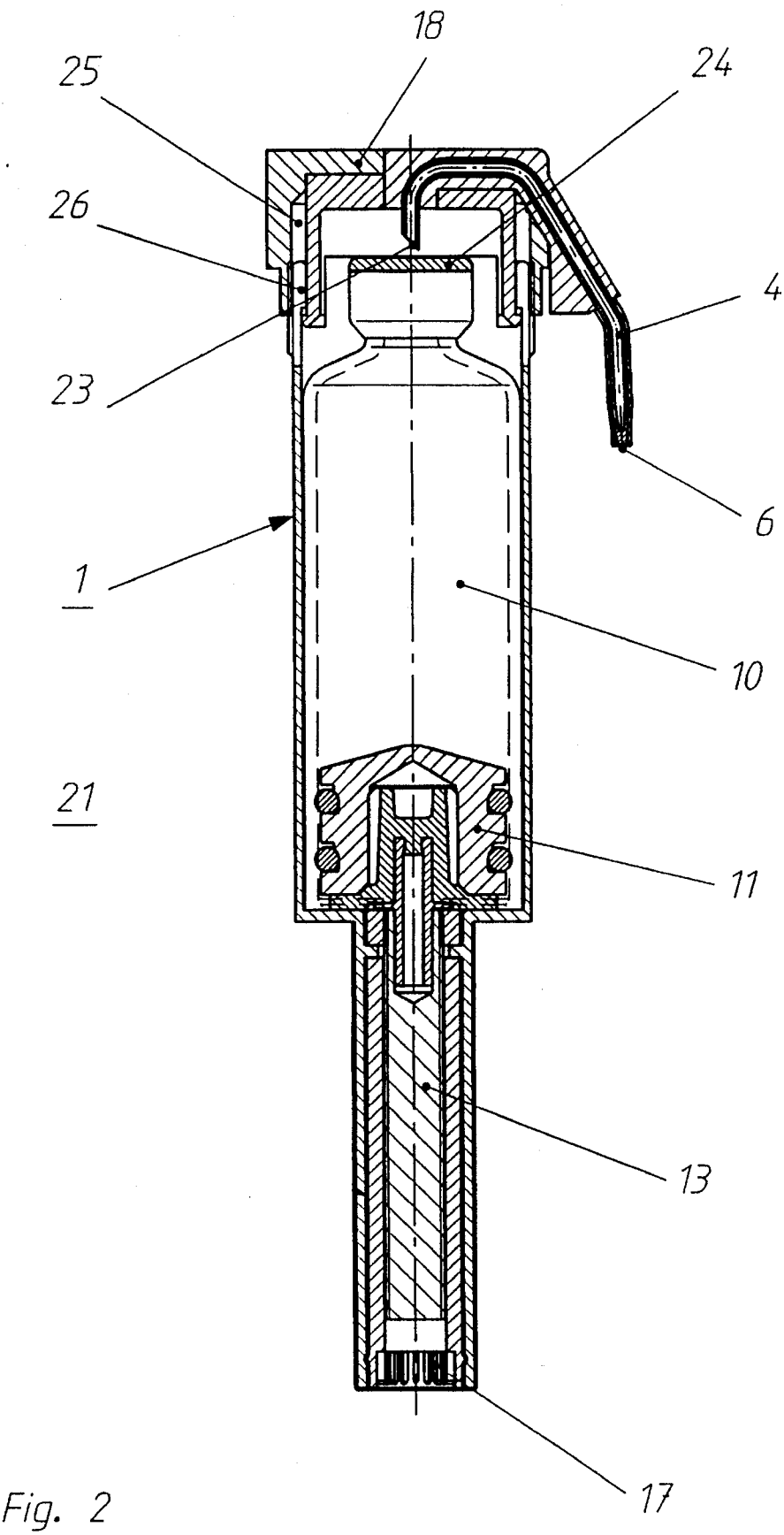
FIG. 2 is a side elevation, in section, of a dosing unit for the inhaler of the invention when activated.
Figure 3:
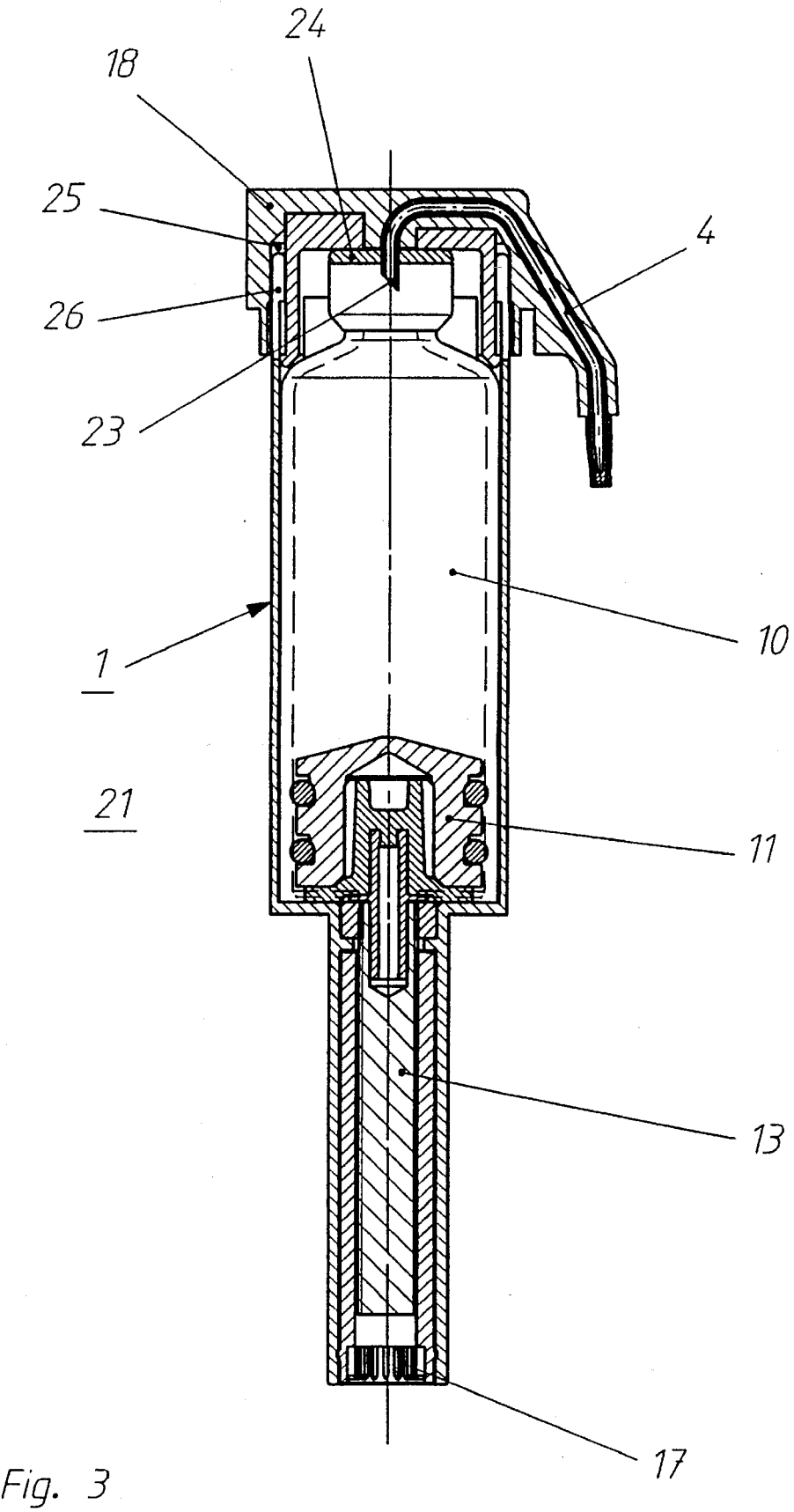
FIG. 3 is a side elevation, in section, of an inhaler of the invention with the dosing unit of FIG. 2 inserted when in its activated state.

Dosing unit 21, shown separately in FIGS. 2 and 3, comprises a reservoir 1 which houses a pre-filled ampoule 10, the ampoule having a movable plunger 11 and containing the liquid medicine, the plunger being entered by one end of a threaded rod 13. An annular pawl 26 of reservoir 1 is inserted into and latches in an annular cavity 25 of an adapter head 18 which carries a feed line 4.

In the inactive position shown in FIG. 2, the pre-filled ampoule 10 still is entirely intact and therefore its shelf life remains undegraded. When, by means of a rotary or translational axial displacement, reservoir 1 containing pre-filled ampoule 10 is forced into annular cavity 25 of adapter head 18, then an ampoule membrane 24 is pierced by an inner end 23 of feed line 4 which points toward reservoir 1 and, as a result, the liquid medicine can flow from ampoule 10 into feed line 4.

Dosing unit 21 thus activated, as shown in FIG. 3, can be inserted in non-rotatable manner into housing 22 (FIG. 1). A geared link 17 at the opposite end of the threaded rod 13 then meshes with an output gear 27 of a drive unit 28 of conveyor 2. Gear 27 in turn meshes with a gear 20 of drive unit 28 which is actuated by power unit 12, preferably an electric motor. The distal outlet end 6 of feed line 4 is positioned in this process through an aperture 27 in a nozzle 19 into an accurately predefined location directly above a vibrator 3.

Vibrator 3 is piezoelectric and generates ultrasonic vibrations. A suitable ultrasonic vibrator is described in European patent document B1 246,515.

As shown by FIG. 1, conveyor 2 comprises power unit 12 and drive unit 28. Two batteries 16 provide energy for both the power unit 12 and the electronic process control means 15. This process control 15, which preferably is a programmable microprocessor, controls power unit 12 and vibrator 3, and its operation is initiated by pressing an actuation button 14 (which in more elaborate applications may be replaced by a keypad).

The European patent document B1 143,895 describes a dosing unit part of the conveyor which is suitable for the inhaler of the invention and which consists of a spindle-nut gear unit of which the output member consists primarily of a drive bushing rotatably resting in the inhaler housing and the output member by the spindle. The drive bushing is coaxial with a fastener for the pre-filled ampoule in the housing and the spindle is coaxially insertable into the drive bushing. Part of the housing adjoining the fastener secures the nut against axial displacement and keeps it non-rotatably in place. The spindle is non-rotatable, but longitudinally displaceable inside the drive bushing so that it can be advanced by drive-bushing rotation into the fastener to directly advance the plunger of a pre-filled ampoule.

Figure 4:
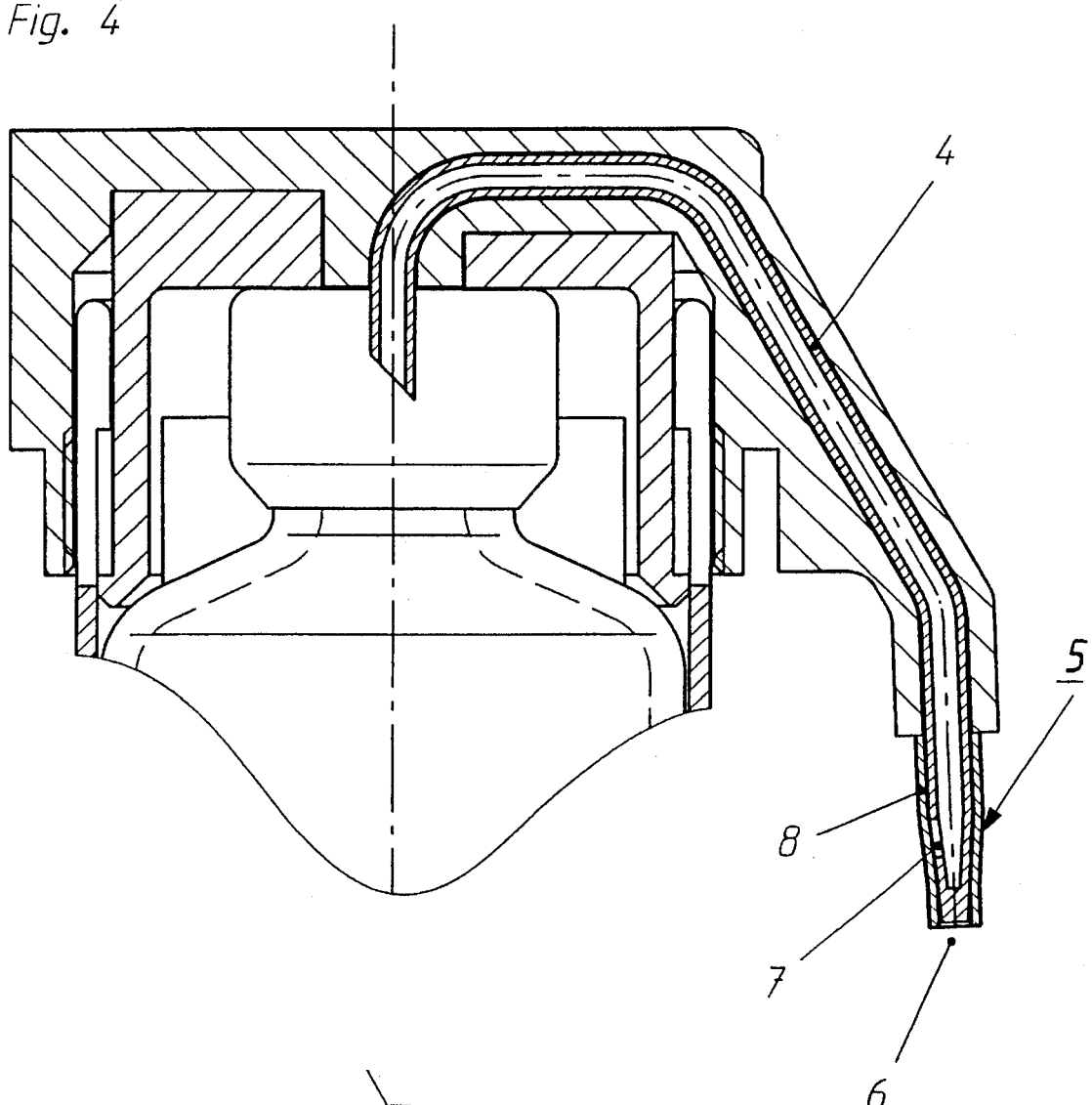
FIG. 4 is an enlarged side elevation, in section, of a feed line of the inhaler of FIG. 3.

The feed line 4 ending directly above the vibrator 3 is sealed in an airtight manner when in the rest position, as shown in FIG. 4. End 6 of feed line 4 facing vibrator 3 is sealed and has only one aperture 7 in the side of the feed line which is sealed by an elastic membrane 8 in the form of a rubber tubing, preferably silicone rubber, slipped over end 6 of the feed line. This combination forms a valve 5 which is automatically closed in the rest state and which opens automatically in the operational state by liquid pressure. When conveyor 2 is actuated, liquid medicine is moved from reservoir 1, through feed line 4 and to vibrator 3. The design of conveyor 2 is such that it generates an operational pressure of 0.01 to 5.00 bars, preferably between 0.5 and 1.0 bars, in the pre-filled ampoule.

Figure 5:
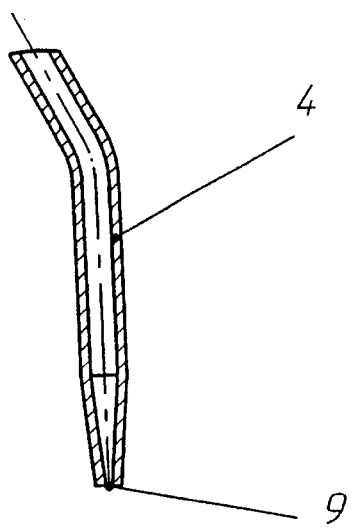
FIG. 5 is an enlarged side elevation, in section, of a capillary embodiment of the inhaler feed line.

FIG. 5 shows an alternative embodiment wherein the end of feed line 4 ending directly above vibrator 3 comprises a capillary discharge aperture 9 through which liquid moved by the conveyor 2 out of reservoir 1 and through feed line 4 is dispensed to vibrator 3.

A patient uses the inhaler in such a way that inhaler nozzle 19 is moved close to the patient's mouth. Pressing an actuation button 14 electrically actuates control processor means 15 and initiates operation of both conveyor 2 (with power unit 12 and drive unit 28) and vibrator 3. Vibrator 3 may be actuated either simultaneously with conveyor 2 or with a positive or negative delay. By means of the two gears 20, 27 and gear connector 17, drive unit 28 drives drive rod 13 which is displaced upwards, axially forcing plunger 11 of ampoule 10 upward and moving liquid medicine into feed line 4. Elastic membrane 8, slipped over end 6 of feed line 4, is radially widened at aperture 7, allowing liquid medicine to discharge and form into a droplet at end 6 of feed line 4, said droplet being atomized by the high-frequency vibrations of vibrator 3 and being released by nozzle 19. By pressing the actuation knob 14 and simultaneously inhaling at the nozzle 19, the lung-destined medicine reaches the patient's respiratory tract in a controlled manner.

When a microprocessor is used as process control means 15, actuation knob 14 can be converted into a multi-function keypad and, where called for, be equipped with programming. In this manner preselected quantities of atomized medicine can be discharged.

On the other hand, different types of dosing units 21 may be employed to dispense different types and quantities of medicines using the same housing 22, the individual dosing units 21 being disposable in such cases.

What is claimed is:

1. A medical inhaler to generate an aerosol of a pharmaceutically effective medication to be absorbed in the respiratory tract of a patient comprising the combination of a reservoir (1) containing a liquid medication;

a dosing unit including means movable within said reservoir;

a conveyor (2) to activate said dosing unit for expelling said liquid medication out of said reservoir (1), an atomizing vibrator (3);

a feed line (4) for conducting said liquid medication from said reservoir (1) to said vibrator (3); and process control means (15) for controlling and coordinating operation of said conveyor (2) and said atomizing vibrator (3).

2. An inhaler according to claim 1, characterized in that the control processor means (15) is a microprocessor.

3. An inhaler according to claim 2 wherein said process control means (15) is programmable.

4. An inhaler according to claim 1 wherein said feed line (4) has an outlet end positioned directly above said vibrator (3), and including an automatically closing valve (5) hermetically sealing said outlet end in a rest position, said valve opening under pressure to dispense onto said vibrator (3) liquid medication moved by said conveyor (2) from said reservoir (1) through said feed line (4).

5. An inhaler according to claim 4 wherein said feed line (4) comprises a tube having a lateral aperture (7) at said outlet end (6) facing said vibrator (3), and wherein said automatically closing valve comprises an elastic tube slipped over said outlet end (6) of said feed line.

6. An inhaler according to claim 4 wherein said outlet end of said feed line (4) comprises a capillary discharge aperture (9) for discharging liquid medication onto said vibrator (3).

7. An inhaler according to claim 1 wherein said vibrator (3) includes a piezoelectric element for generating ultrasonic flexural vibrations.

8. An inhaler according to claim 1 wherein said reservoir (1) comprises a pre-filled ampoule (10) with a movable plunger (11) in said ampoule.

9. An inhaler according to claim 8 and including a gear drive unit (28) having an output gear (27), a threaded rod (13) having one end attached to said plunger and an opposite end coupled said output gear of said gear drive unit (28).

10. An inhaler according to claim 9 and further comprising a housing (22) containing said conveyor (2), said vibrator (3) and said process control means (15), and wherein said reservoir (1), said pre-filled ampoule (10), said feed line (4), said threaded rod (13) and said connecting gear (17) are assembled as a separate dosing unit (21) separately insertable into and removable from said housing.

11. An inhaler according to claim 8 wherein said ampoule has a membrane (24) across an open end thereof, said reservoir (1) containing said ampoule (10) includes an adapter head (18) enclosing said feed line (4), said adapter head being coupled to said reservoir and being movable so that an inlet end (23) of said feed line (4) faces said reservoir and pierces said membrane (24) to permit liquid medicine to flow from said ampoule into said feed line.

12. An inhaler according to claim 1 wherein said conveyor (2) and said vibrator (3) are actuated simultaneously.

13. An inhaler according to claim 1 wherein said conveyor (2) actuation is time delayed relative to actuation of said vibrator (3).

14. An inhaler according to claim 1 wherein said vibrator (3) actuation is time delayed relative to actuation of said conveyor (2).

15. A medical inhaler to generate an aerosol of a pharmaceutically effective medication to be absorbed in the respiratory tract of a patient comprising the combination of a reservoir (1) containing a liquid medication;

a dosing unit including means movable within said reservoir;

a conveyor (2) to acute said dosing unit for expelling said liquid medication out of said reservoir (1), an atomizing vibrator (3);

a feed line (4) for conducting said liquid medication from said reservoir (1) to said vibrator (3), said feed line having an outlet end adjacent said vibrator including an automatically closing valve hermetically sealing said outlet end in a rest position; and process control means (15) for controlling operation of said conveyor (2) and said atomizing vibrator (3) and coordinating delivery of liquid medication through said feed line to said vibrator.

* * * * *